United States Patent
Lassila et al.

(10) Patent No.: US 12,403,073 B2
(45) Date of Patent: Sep. 2, 2025

(54) DENTAL MATERIAL

(71) Applicant: Stick Tech Oy, Turku (FI)

(72) Inventors: Lippo Lassila, Lielax (FI); Sufyan Garoushi, Turku (FI); Pekka Vallittu, Kuusisto (FI); Eija Sailynoja, Littoinen (FI)

(73) Assignee: Stick Tech Oy (FI)

( * ) Notice: Subject to any disclaimer, the term of this patent is extended or adjusted under 35 U.S.C. 154(b) by 748 days.

(21) Appl. No.: 17/627,062

(22) PCT Filed: Jul. 23, 2020

(86) PCT No.: PCT/FI2020/050501
§ 371 (c)(1),
(2) Date: Jan. 13, 2022

(87) PCT Pub. No.: WO2021/019128
PCT Pub. Date: Feb. 4, 2021

(65) Prior Publication Data
US 2022/0273523 A1    Sep. 1, 2022

(30) Foreign Application Priority Data
Jul. 26, 2019  (EP) ..................................... 19188496

(51) Int. Cl.
*A61K 6/887*  (2020.01)
*A61C 5/20*   (2017.01)
(Continued)

(52) U.S. Cl.
CPC ................ *A61K 6/887* (2020.01); *A61C 5/20* (2017.02); *A61C 13/0022* (2013.01); *A61K 6/836* (2020.01)

(58) Field of Classification Search
CPC .......... A61K 6/887; A61K 6/836; A61K 6/76; A61K 6/77; A61K 6/75; A61C 5/20; A61C 13/0022
See application file for complete search history.

(56) References Cited

U.S. PATENT DOCUMENTS

| 5,266,609 A | 11/1993 | Hall et al. |
| 9,714,396 B2 * | 7/2017 | Feng ....................... A61Q 15/00 |
| 2014/0131908 A1 * | 5/2014 | Sun ..................... A61C 13/0013 264/16 |

FOREIGN PATENT DOCUMENTS

| EP | 2959882 A1 | 12/2015 |
| WO | WO-2015197679 A1 * | 12/2015 ........... A61K 6/0008 |

OTHER PUBLICATIONS

Garoushi et al., "Mechanical Properties and Radiopacity of Flowable Fiber-reinforced Composite," Dental Materials J. 2019; 38, 196-202.

* cited by examiner

Primary Examiner — Robert S Jones, Jr.
Assistant Examiner — Zhen Liu
(74) Attorney, Agent, or Firm — Timothy H. Van Dyke; Wolter Van Dyke Davis, PLLC (57) ABSTRACT

The invention relates to a dental material comprising a polymer resin, particulate fillers and randomly oriented inorganic fibres, wherein an average largest dimension of the particulate fillers is 0.3-1.2 µm, the inorganic fibres have a diameter of 4-8 micrometre and an aspect ratio of 20-80 based on an average length of the inorganic fibres and the dental material is void of other fibres. Additionally, the total amount of particulate fillers and inorganic fibres is 70-85 wt-% of the total weight of the material, and the amount of inorganic fibres is 20-35 wt-% of the total amount of particulate fillers and inorganic fibres.

12 Claims, 7 Drawing Sheets

(51) Int. Cl.
*A61C 13/00* (2006.01)
*A61K 6/836* (2020.01)

DENTAL MATERIAL

FIELD OF THE INVENTION

The invention relates to a dental material comprising a polymer resin, particulate fillers and randomly oriented inorganic fibres, having a suitable viscosity to give it good handling and manipulation properties.

BACKGROUND AND SUMMARY OF THE INVENTION

Various fibre-reinforced composite materials are known in the art. Despite the numerous materials known, there still exists a need for providing a composite material, especially for dental uses that has a suitable viscosity while at the same time leading to a product with good mechanical properties, such as strength. By suitable viscosity it is meant a material that has good handling and manipulation properties, namely a material that flows easily to each corner of a dental cavity to be filled with said material.

In dental applications, composite materials are also used as restorative materials. In such applications, the composite material is surrounded by the natural tooth, i.e. by dentin and enamel. It would be preferable if the mechanical properties of the restorative material were either similar or better than those of enamel and dentin.

An object of the invention is to minimise or even totally eliminate the disadvantages existing in the prior art. It is thus an object of the invention to provide a dental material that has good handling and manipulation properties, while still having sufficient filler content to have good mechanical properties such as strength.

DETAILED DESCRIPTION

The present description relates to a dental material comprising a polymer resin, particulate fillers and randomly oriented inorganic fibres. In a typical dental material
  an average largest dimension of the particulate fillers is 0.3-1.2 µm,
  the inorganic fibres have a diameter of 4-8 micrometre and an aspect ratio of 20-80 based on an average length of the inorganic fibres,
  the dental material is void of other fibres,
  the total amount of particulate fillers and inorganic fibres is 70-81 wt-% of the total weight of the material, and
  the amount of inorganic fibres is 20-35 wt-% of the total amount of particulate fillers and inorganic fibres.

One of the most important properties of clinical usability of dental filling materials is an optimum viscosity, which allows the filling material to be easily applied to a dental cavity. Typically, the handling properties are defined by adjusting the ratio of monomer matrix and filler, The present invention relates to an unexpected viscosity behaviour of fibre-reinforced dental material, which allows a high filler content with good handling and manipulation properties. A high filler content is indeed required also to achieve good mechanical properties.

The present dental material thus has surprisingly both good handling properties and good mechanical properties, as will be demonstrated in the Experimental section below. This is believed to be the result of the combination of the specific diameter fibres with the specific aspect ratio, and the amount of inorganic fillers with respect to the amount of the fibres.

The percentages in this description are weight-percentages (wt-%) of the total weight of the material, unless otherwise stated, The aspect ratio is equal to the ratio of length to diameter, i.e. a fibre having a length of 140 micrometre and a diameter of 6 micrometre has an aspect ratio of 23.3. By total filler content it is meant the combined amounts of particulate fillers and inorganic fibres. The terms particulate fillers and particle fillers and particles are used interchangeable, and whenever fibres are mentioned, the inorganic fibres are meant.

The polymer resin is preferably in its uncured form in the composite material before its application, and is cured once it is placed into its final position (such as in a dental cavity to be restored). By curing, it is meant either polymerisation or cross-linking or similar. The curing may be induced by light, heat or by a combination of an initiator/activator and light (called dual curing), or other external energy like wave energy such as UV or ultrasonic activation.

Since the polymer resin (which may also be called the matrix material) is in its uncured form, the composite material may also be called a prepreg, i.e. a prepreg is an uncured composite, i.e. it contains all the components of the finished composite material, but the polymer resin is still in monomer form, or when a crosslinkable resin is used, in its non-crosslinked form.

The inorganic fibres have a diameter of 4-8 micrometre, i.e. they have a diameter from 4, 4.5, 5, 5.5, 6, 6.5 or 7 µm up to 5, 5.5, 6, 6.5, 7, 7.5 or 8 µm. The aspect ratio of the inorganic fibres is 20-80 based on an average length of the inorganic fibres, i.e. the aspect ratio can be from 20, 25, 30, 35, 40, 45, 50, 55, 60, 65 or 70 up to 30, 35, 40, 45, 50, 55, 60, 65, 70, 75 or 80. It is important to note that there are no other fibres in the dental material, i.e. other fibres are absent from the dental material.

The total amount of particulate fillers and inorganic fibres is 70-81 wt-% of the total weight of the material. The total amount of fillers and fibres is thus from 70, 72, 75, 78 or 80 wt-% up to 72, 75, 78, 80 or 81 wt-% of the total weight of the material. The rest of the dental material is thus in majority the polymeric material. Indeed, some additives (such as pigments or a fluorescent material) can be added (as explained in more detail below), but their total content is typically at most 3 wt-%, more typically at most 0.1 wt-% of the total weight of the material.

The amount of inorganic fibres is 20-35 wt-% of the total amount of particulate fillers and inorganic fibres, i.e. there are more particulate fillers in weight than of the fibres. The amount of inorganic fibres can be from 20, 22, 25, 27, 30 or 32 wt-% up to 22, 25, 27, 30, 32 or 35 wt-% of the total amount of particulate fillers and inorganic fibres.

According to an embodiment, the inorganic fibres are selected from the group consisting of inert glass fibres (for example E-, ECR-, C-, S-, AR-, HM-, A- or D-glass fibres), basalt glass fibres, bioactive glass fibres, sol-gel processed silica fibres, aluminium oxide based fibres, zirconia fibres, apatite fibres, quartz fibres and mixtures thereof. According to a preferred embodiment, the inorganic fibres are inert glass fibres.

According to an embodiment, the fibres of the fibre material are at least partly, sometimes even fully, silanated, i.e. surface treated such that at least a majority of their outer surface is covered with a silane component. It is also possible that the fibres become partly silanated, since the fibres are fully silanated when they are added to the composite material mixture, but as they slightly break into shorter fibres during the mixing of the ingredients, the ends of the shorter fibres are no longer silanated. It is also possible that the fibre material comprises a mixture of silanated and non-silanated fibres. According to an embodiment, at least 90% of the surfaces of the fibres in the fibre material are silanated. The silanation is such that it is compatible with the resin used as the matrix material, i.e. it contains active groups such as vinyl groups, acrylate groups, methacrylate groups or epoxy groups.

The fibres of the fibre material can thus be surface treated to enhance their bonding to the surrounding matrix material. The methods of surface treatment as well as the surface treating agents used may vary depending on the fibre material. The fibre material can be functionalised with e.g. hydroxyapatite, silanate, titanate, zirconate, chromium complexes or aluminate. The fibre material may thus be both silanated and have another surface treatment.

According to another embodiment, the average length of the inorganic fibres is 100-200 µm. The average length can thus be from 100, 110, 120, 130, 140, 150, 160, 170 or 180 µm up to 120, 130, 140, 150, 160, 170, 180, 190 or 200 µm.

In context of the present application the average length of the fibres is determined as follows. The fibres are divided into a number of fractions with 0.1 mm intervals according to their length. The fibre lengths in each 0.1 mm interval are added together. The average fibre length is taken to be value where the lengths of the shorter fibres and longer fibres are deemed to be the same. A typical median fibre length is for example 100 µm with standard deviation 130 distribution.

According to a preferred embodiment, the polymer resin is a methacrylate-based polymer resin. The methacrylate-based polymer resin may be for example selected from a group consisting of homopolymers and copolymers of methyl methacrylate, ethyl methacrylate, n-butyl methacrylate, isobutyl methacrylate, 2-ethylhexyl methacrylate, 2-hydroxyethyl methacrylate, cyclohexyl methacrylate, isobornyl methacrylate, tetrahydrofurfuryl methacrylate, benzyl methacrylate, morpholinoethyl methacrylate, acrylic add, diethylene glycol dimethacrylate, triethylene glycol dimethacrylate (TEGDMA), diurethane dimethacrylate, urethane dimethacrylate (UDMA), 2,2-bis(4-(2-hydroxy-3-methacryloxy)phenyl)-propane (BisGMA), ethoxylated bisphenol-A dimethacrylate (BisEMA) or ethoxylated urethane dimethacrylate (ethoxylated UDMA). A mixture of urethane dimethacrylate and triethyleneglycol dimethacrylate is one particularly good polymer resin for the present dental material, for example consisting of 65-75 wt-% of urethane dimethacrylate and 25-35 wt-% of triethyleneglycol dimethacrylate.

The dental material also comprises required and suitable initiators and activators (commonly named initiators), such as caniphorquinone, to induce curing of the polymer resin.

Any dental fillers, i.e. fillers used in dentistry can be used in the present dental material. According to an embodiment, the particulate fillers (also called particle fillers or fillers in this description) are selected from the group consisting of inert glass, colour pigments, inert or bioactive or partially reactive glass ionomer fillers containing elements selected from Si, Al, Ca, P, Ba, Mg, K, Ti, F, Sr, Zn oxides or other compounds of said elements, colour pigments, inter ceramics, hydroxyl apatite or other Ca-phosphates, $Al_2O_3$, $ZrO_2$, Ag, Al—Si oxides, feldspar, zerogels, bioactive glasses or filler particles containing functional bioactive or therapeutically active molecules and/or radio-opaque materials. Pigments are typically organic pigments or dyes, but also metal oxides can be used. Preferably the particulate filler material is inorganic filler material. The particulate filler material is typically selected such that it gives to the finished composite material its desired colour and radio-opacity.

By particles, it is meant also for example spheres and very short fibres (where the length of the fibre is at most two times its diameter, i.e. the aspect ratio is at most 2). The average largest dimension of the particulate fillers is 0.3-1.2 µm. The diameter of the particles in the filler material is thus, in the case of irregular particles, the largest diameter of the particles. The diameter can be from 0.3, 0.4, 0.5, 0.6, 0.7, 0.8, 0.9 or 1 µm up to 0.5, 0.6, 0.7, 0.8, 0.9, 1, 1.1 or 1.2 µm. The present dental material is thus typically essentially void of larger filler particles, i.e. it does not contain filler particles having an average largest dimension which is above 1.2 µm. As the particles can be manufactured for example by crushing and sieving, it is not impossible that it contains a few particles that are larger than 0.3-1.2 µm, but the amount of such larger (or smaller) particles is negligible.

The present dental material may also comprise an amount of smaller particles, namely particles having an average largest dimension of 10-50 nm. These particles are typically silica particles, silanated or untreated. Their amount is typically less than 2-3 wt-%, for example 0.5 wt-% or less.

The dental material may also further comprise growth factors, antigens, antibiotics, disinfectants, bone morphogenic proteins (BMPs), interferons, corticosteroids, bisphosphonates, cytostatics, anabolic hormones, vitamins, anti-inflammatory agents, antimicrobiotics and combinations and mixtures thereof.

The present description relates also to a use of a dental material as described above as dental filling material, as prosthodontic material and for manufacturing CAD/CAM blocks to be used in dentistry.

The dental material described above, and all its variants, may thus be used as dental filling material or as a dental cement. It may also be used as prosthodontic material, for example for periodontal splinting, as crown and bridge material, as post and core materials, as endo-crown materials or for a pontic in fixed partial dentures. It may be used either in direct use (i.e. directly to the patient's mouth) or in indirect use (in laboratory). It may also be used as orthodontic retainer material.

One beneficial use of the material is for manufacturing CAD/CAM-blocks. Indeed, the present material is easy to arrange in a mould without any bubbles of air, because of its viscosity. In such use, the material is preferably cured with heat and not with light.

DETAILED DESCRIPTION OF DRAWINGS

Figure 1:
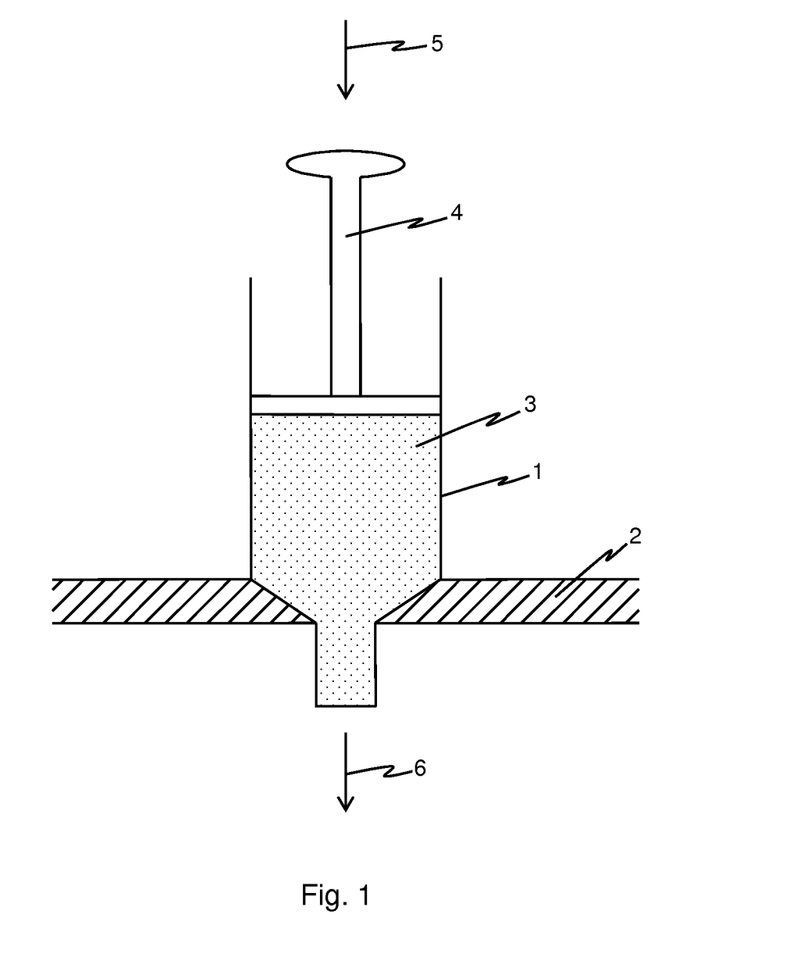
FIG. 1 is a schematic illustration of a device for measuring extrusion force.

FIG. 1 illustrates a measurement device used for measuring the stress needed for extrusion. The device consists of a standardised 5 ml syringe 1, which is secured to a support 2. The dental material to be tested is arranged into the syringe, into space 3, and pushed out of the syringe (into the direction of arrow 6) by using a piston 4. The force required in the direction of arrow 5 is measured and gives a dose estimation of extrusion force.

EXPERIMENTAL PART

Some dental materials were prepared and tested.

The inorganic fibres were inert glass fibres having a diameter of 6 μm and a length of 50-200 μm with an average length of 150 μm (aspect ratio 25). The particulate fillers were SiO$_2$,BaO (Schott G018-053, surface treated) and had an average diameter of 0.7 μm.

The polymer resins used were the following.
- urethane dimethacrylate (MDMA), CAS Number 72869-86-4, from Sigma-Aldrich
- triethylene glygol dimethacrylate (TEDGMA) from Sigma-Aldrich
- 2,2-bis(4-(2-hydroxy-3-methacryloxy)phenyl)-propane (BisGMA) from Esstech Inc
- bis-phenol A ethoxylate dimethylacrylate with n+m=3 (BisEMA) from Esstech Inc Camphorquinone (CQ, Sigma-Aldrich) was used as a light initiator and DMAEMA-tertiary amine ((dimethylamino)ethyl methacrylate-tertiary amine) as an activator (both being initiators). Their weight was thus negligible.

Table 1 gives a first set of dental materials prepared. The particle:fibre ratio was kept at a constant 2:1, and the amount of polymer resin was varied. The polymer resin was 70 wt-% of UDMA (urethane dimethacrylate) and 30 wt-% of TEDGMA (triethylene glygol dimethacrylate).

TABLE 1

| Polymer (g) | Particle fillers (g) | Fibres (g) | Initiators (wt-%) | Total filler content (wt-%) |
|---|---|---|---|---|
| 11 | 20 | 10 | <1 | 73 |
| 10 | 20 | 10 | <1 | 75 |
| 9 | 20 | 10 | <1 | 77 |
| 8 | 20 | 10 | <1 | 79 |
| 7 | 20 | 10 | <1 | 81 |
| 6 | 20 | 10 | <1 | 83 |

Some further dental materials were prepared according to the amounts given in Table 2. The polymeric resins were the following (i.e, each combination was prepared with each resin)
- 70 wt-% of UDMA and 30 wt-% of TEGDMA
- 60 wt-% of BisGMA and 40 wt-% of TEGDMA
- 40 wt-% of BisEMA, 35 wt-% of UDMA and 25 wt-% of TEGDMA

TABLE 2

| Total amount of particles and fibres (wt-%) | Fibres (wt-%) | Polymer resin (wt-%) |
|---|---|---|
| 75 | 0 | 25 |
| 75 | 10 | 25 |
| 75 | 15 | 25 |
| 75 | 20 | 25 |
| 75 | 22 | 25 |
| 75 | 25 | 25 |
| 75 | 27 | 25 |
| 75 | 30 | 25 |
| 78 | 21 | 22 |
| 78 | 26 | 22 |
| 78 | 31 | 22 |
| 79 | 21 | 21 |
| 79 | 23 | 21 |
| 79 | 26 | 21 |
| 79 | 29 | 21 |
| 79 | 31 | 21 |
| 80 | 24 | 20 |
| 80 | 27 | 20 |
| 80 | 29 | 20 |
| 80 | 32 | 20 |

The dental materials were prepared using the amounts given in Tables 1 and 2. Firstly, the polymer resins were mixed and the initiators CQ and DMAEMA were added to the mixture, Once a homogenous liquid was achieved, the particles and fibres were added and mixed using Speedmixer until homogenous composite paste was achieved (typically thrice 30 seconds). Finally, the dental material was vacuumed using a Thinky vacuum mixer and the material was inserted to a standard 5 ml syringe (Terumo).

A viscosity test was carried out using an extrusion test with syringe using universal testing device with fixed push-out speed (5 mm/min), as shown in FIG. 1. The extrusion force (N) was measured and pushout force was registered at end of test.

Results of viscosity tests for different dental resins are given in FIGS. 2-6.

Figure 2:
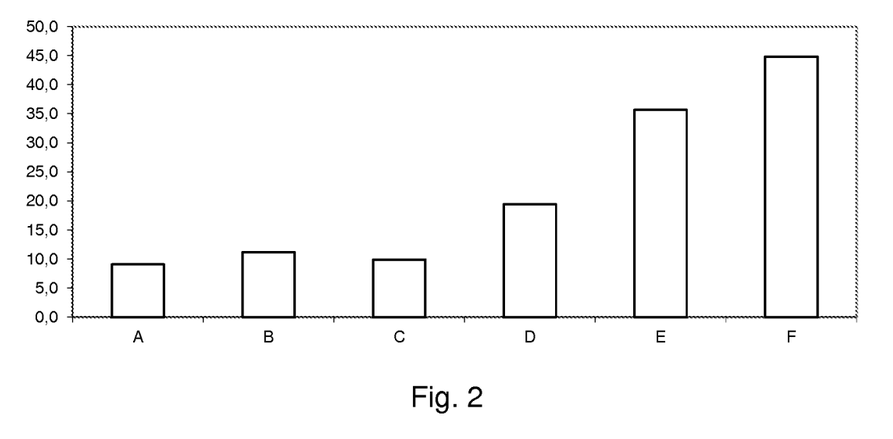
FIGS. 2-6 are graphs illustrating results of viscosity tests.

FIG. 2 illustrates the extrusion force (in N) using the resin of 70 wt-% of UDMA and 30 wt-% of TEGDMA, with a total content of fibres and particles (total filler content) varying from 73 wt-% to 81 wt-%. The particle:fibre-weight ratio was fixed at 2:1. The sample A had a total filler content of 73 wt-%, sample B 75 wt-%, sample C 77 wt-%, sample D 79 wt-%, sample E 80 wt-%, sample F 81 wt-%.

When the total filler content reached 79 wt-%, the extrusion force was increasing rapidly. A sample with 83 wt-% total filler content was not measurable by extrusion test.

Figure 3:
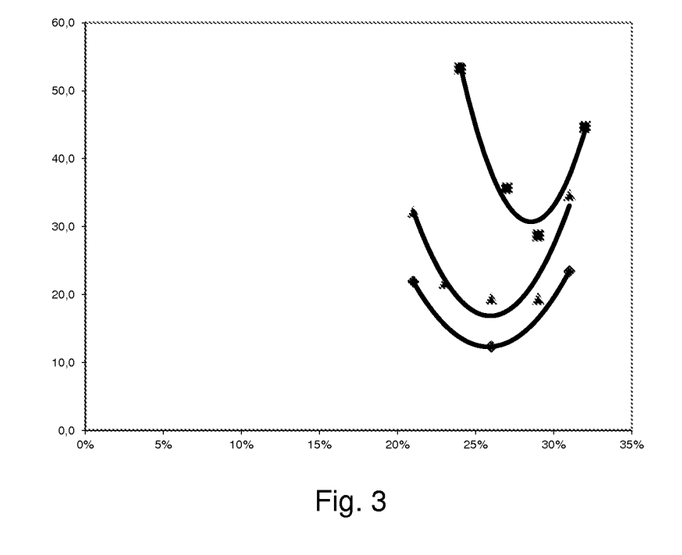

FIG. 3 illustrates the effect of the particle:filler-ratio on viscosity. The abscissa indicates the amount of fibres (in wt-%) and the ordinate the extrusion force, Samples with fixed total filler content of 78 wt-%, 79 wt-% and 80 wt-% were tested. The polymer resin used was 70 wt-% UDMA and 30 wt-% TEGDMA. In FIG. 3, the lowest curve gives the extrusion force for a material with a total filler content of 78 wt-%. The middle curve gives the extrusion force for a material with a total filler content of 79 wt-% and the uppermost curve gives the extrusion force for a material with a total filler content of 80 wt-%.

From FIG. 3, it can be seen that when the amount of particles was increased, viscosity increased. Also, when the amount of fibres was increased, viscosity increased rapidly. However, there was certain ratio of particles to fillers which is dose to 2.1, where viscosity rapidly decreases (as shown as the lowest point in each curve). Thus, the present dental material, with its carefully selected components and their amounts, provides a material which has high total filler content but is still easy to apply and manipulate.

Figure 4:
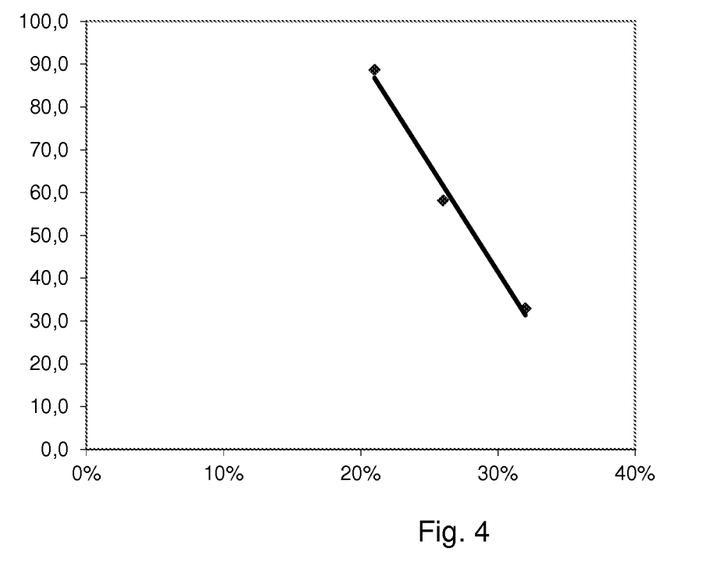

FIG. 4 shows the viscosity (in N on the ordinate) for a dental material comprising particles having an average diameter of 0.7 μm and particles having an average diameter of 5 μm, with a total filler content fixed at 79 wt-%. The amount of the larger particles is indicated on the abscissa (in wt-%). The polymer resin was 70 wt-% of UDMA and 30 wt-% of TEGDMA, and the material did not contain any fibres.

The results show that even though the particles that were added had a similar diameter than the fibres used, the effect on viscosity shown in FIG. 3 was not observed.

Figure 5:
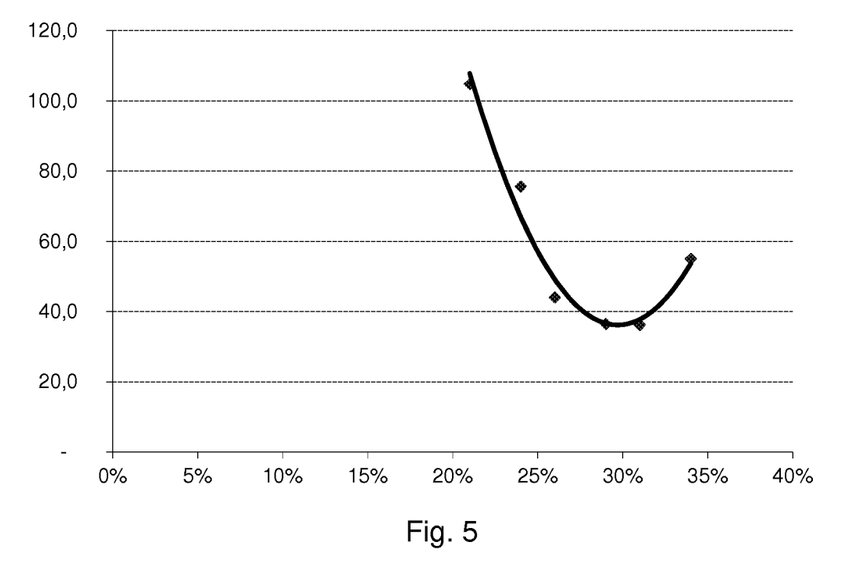

FIG. 5 shows the extrusion force (N, on ordinate) of a dental resin consisting of 60 wt-% of BisGMA and 40 wt-% of TEGDMA with a total amount of fillers being 79 wt-%.

Figure 6:
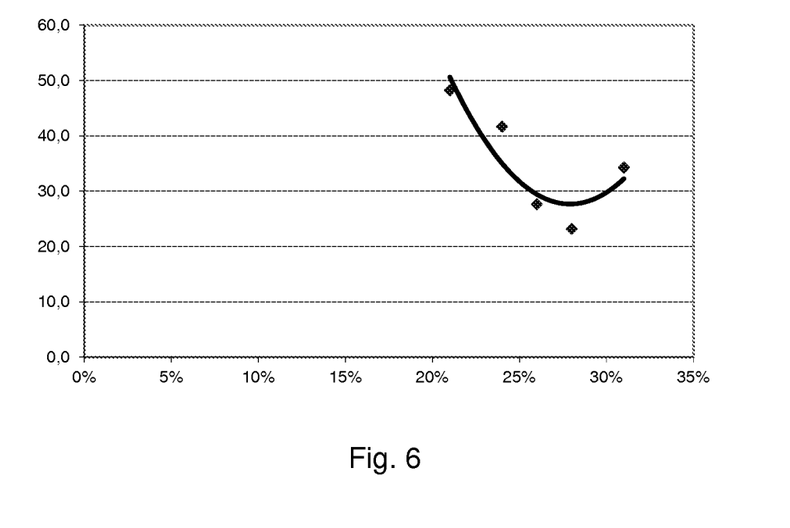

The amount of fibres was varied as is shown on the abscissa in wt-%. FIG. 6 shows the extrusion force (N, on ordinate) of a dental resin consisting of 35 wt-% of UDMA, 40 wt-% of BisEMA and 25 wt-% of TEGDMA with a total amount of fillers being 79 wt-%. The amount of fibres was varied as is shown on the abscissa in wt-%.

Both FIGS. 5 and 6 show the same effect of the fibres on viscosity as FIG. 3. The effect is thus not dependent on a single polymer resin but is present with different polymer resins.

A further extrusion test was carried out using commercial dental composite everX Posterior (GC Corp) having 12-wt-% of fibres and 65 wt-% of particles. The length of the fibres was 600-800 µm (i.e. significantly higher than in the above examples) and their diameter was 17 µm. The aspect ratio was thus between 35 and 47, while the fibres had a larger diameter than in the present dental material. The resulting extrusion force was 200 N, which shows that long fibres increase the required extrusion force significantly.

Mechanical properties of the dental materials were also tested. A three-point bending test (ISO 4049, 2009) was used.

Radio-opacity of the dental resins was also tested using digital method. The specimens were photographed with the dental X-Ray machine from Planmeca. The images were taken digitally with using an X-ray sensor. The program used in taking the pictures was Romex (Planmeca, Tube housing assembly, type: Planmeca intra, serial no: ITHa50320, tube type D-0711SB, manufactured 2005-10, manufactured by Planmeca Oy, Helsinki, Finland). The specimens were set on the X-ray sensor along with the aluminium stairs to get the grey scale for the calculation. The aluminium stairs had heights from 1.0 mm to 8.0 mm. The specimens were photographed by using the following settings: 63 kV, 8 mA and 0.08 s. Using image analysis, grey-scale from the aluminium-stairs was calculated and then for the specimen. By using the equations calculated from the aluminium-stairs grey-values were the values for the specimens determine. As an extra control, a commercial resin (G-aenial Flo X from GC) was used.

The results are given in FIGS. 7-11.

Figure 7:
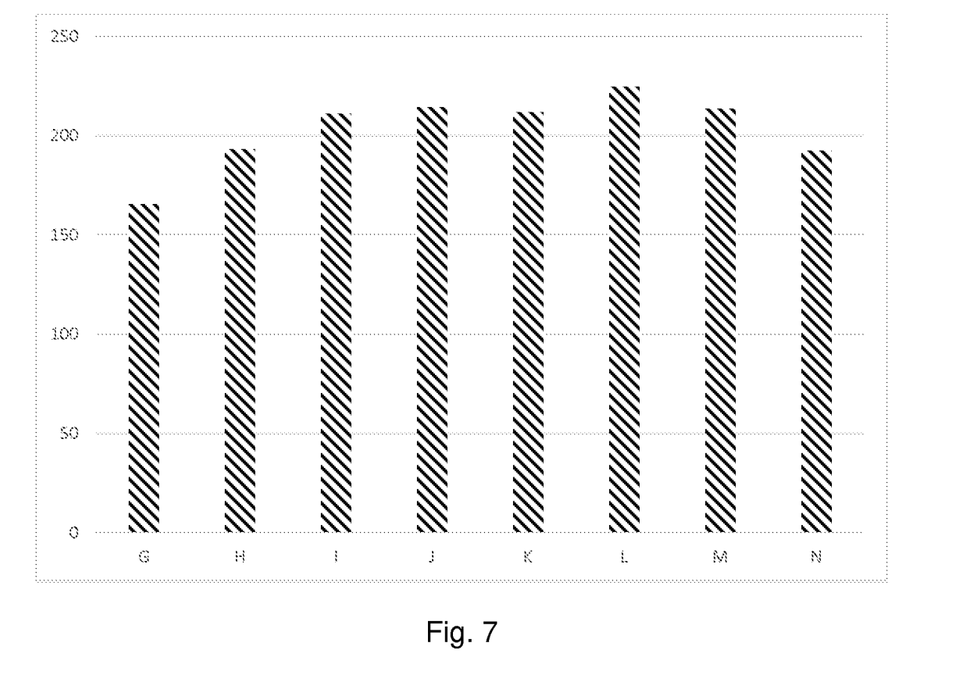
FIGS. 7-13 are graphs illustrating results of mechanical tests.

FIG. 7 shows the effect of filler content on the bending strength (on the ordinate, in MPa). The resin used was UDMA/TEGDMA (70/30) and the total amount of fillers was 75 wt-%. The amount of fibres varied from 0 to 30 wt-% (sample G 0 wt-%, H 10 wt-%, I 15 wt-%, J 20 wt-%, K 22 wt-%, L 25 wt-%, M 27 wt-% and N 30 wt-%).

Figure 8:
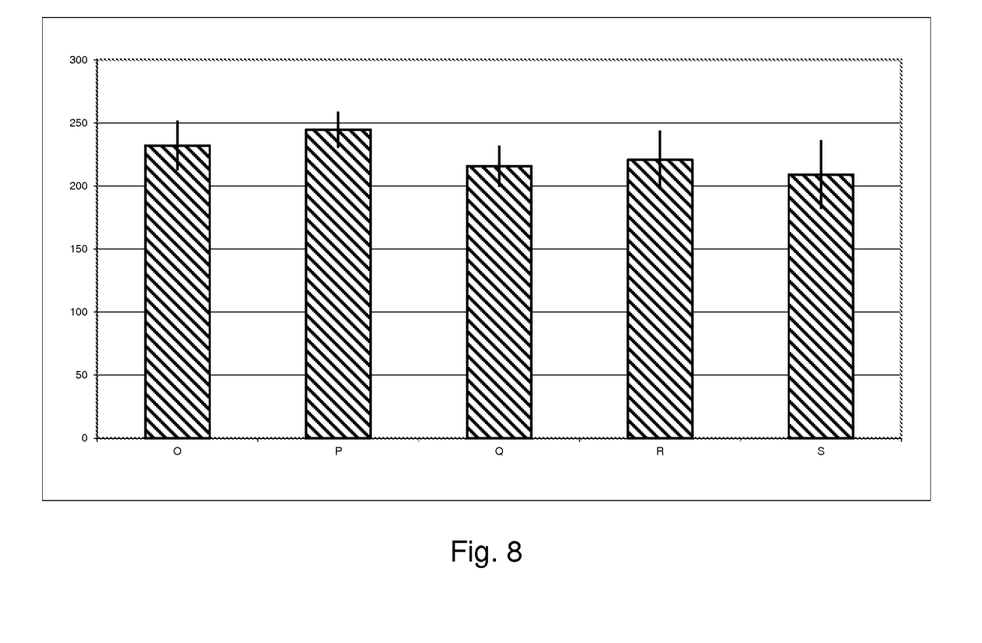

FIG. 8 shows the effect of filler content on the bending strength (on the ordinate, in MPa). The resin used was UDMA/TEGDMA (70/30) and the total amount of fillers was 79 wt-%, while the amount of fibres varied.

In sample O (79%-21%), the amount of fibres was 21 wt-% of the total amount of fillers, in sample P 23 wt-% (79%-23%), sample Q 0 wt-% (79%), sample R 29 wt-% (79%-29%) and in sample S 31 wt-% (79%-31%).

From the graphs 7 and 8, it can be seen that materials with low fibre content have also low mechanical properties, but also too high fibre content decreases the mechanical properties. Surprisingly, the best mechanical properties (highest bending strength) were achieved for those materials for which the viscosity was the lowest.

Figure 9:
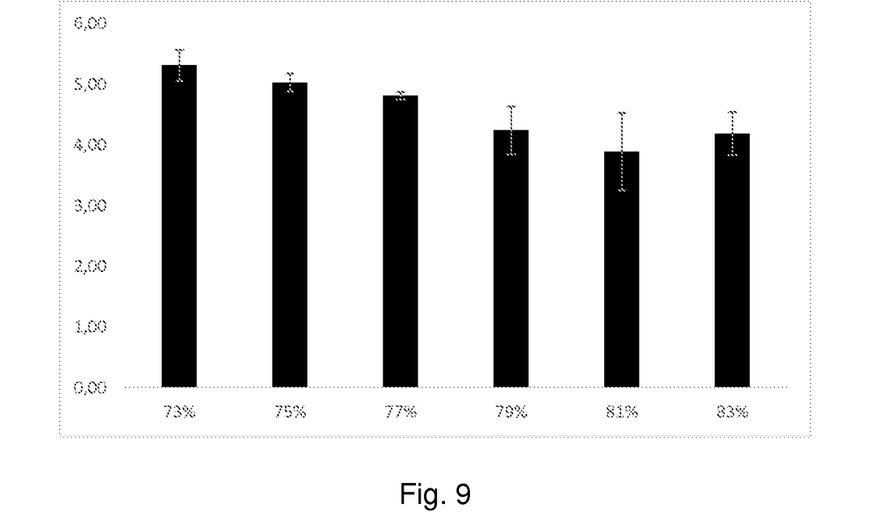

FIG. 9 shows the shrinkage stress (in MPa) when the total filler content (in wt-%) increases.

Shrinkage stress measurement: Glass fibre-reinforced composite (FRC) rods 4 mm diameter and 4 cm in length, had one of their flat surfaces ground with 180 grit silicon carbide sand paper. Two FRC rods were attached tightly to a universal testing machine (model LRX, Lloyd Instruments Ltd., Fareham, England) and resin composite was applied between the FRC rod surfaces. The height of the specimen was set at 2 mm. Two light units (Elipar™ S10, 3M ESPE, Germany) were used simultaneously for 20 s with the tips in close contact with the resin composite specimen from both sides. Shrinkage forces were monitored for 5 min at room temperature (22° C.). Shrinkage stress was calculated by dividing the shrinkage force by the cross-section area of the FRC rod. The maximum shrinkage stress (PS) value was taken from the plateau at the end of the shrinkage stress/time curve. Five specimens were tested for each experimental resin composite.

The sample a has a total filler content of 73 wt-%, sample b 75 wt-%, sample c 77 wt-%, sample d 79 wt-%, sample e 81 wt-% and sample f 83 wt-%. The resin used was UDMA/TEGDMA and the ratio of particles:fibres was 2:1 (in weight), while the total filler amount was increased. As can be seen, the addition of fillers decreases the polymerisation shrinkage stress.

Figure 10:
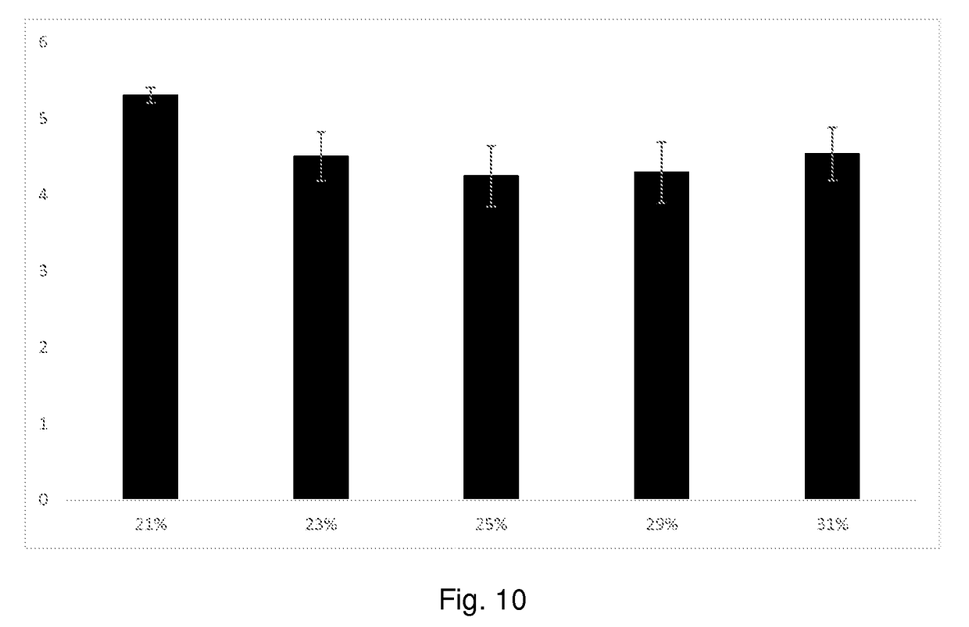

FIG. 10 shows the shrinkage stress (in MPa) where the total amount of filler is constant, but the ratio particles:fibres changes. Indeed, in these tests, the total filler content (in wt-%) was fixed at 79 wt-% and the ratio of particles:fibres was changed. The sample g has a fibre content of 21 wt-%, sample h 23 wt-%, sample i 25 wt-%, sample j 29 wt-% and sample k 31 wt-%. The resin used was UDMA/TEGDMA. As can be seen, the addition of fibres up to a certain amount decreases the polymerisation shrinkage stress. The optimum ratio of particles:fillers is approximately about 2:1.

Figure 11:
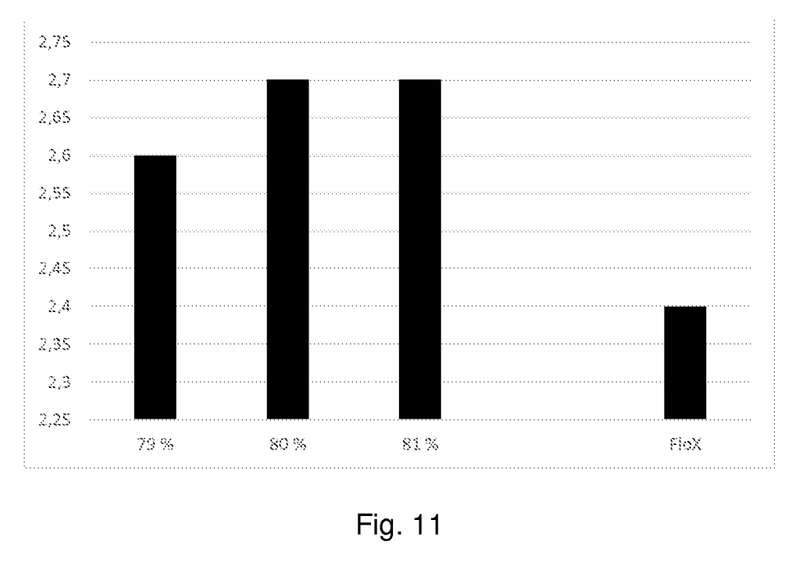

FIG. 11 shows the radio-opacity of a dental material consisting of polymer resin of 70 wt-% UDMA and 30 wt-% TEDGDMA, with a total filler content of 79 wt-% (sample X), 80 wt-% (sample Y) and 81 wt-% (sample Z). The ratio of particles to fibres was 2:1 for the fillers. The rightmost column shows the results for the commercial dental material G-aenial Flo X from GC. The results show that the radio-opacity of the present dental material was better than that of the comparative material.

Some exemplary composite mixtures are given below.

A composite mixture consisting of fillers with a total filler content of 79 wt-% (53 wt-% of particles, 26 wt-% of fibres) and of 21 wt-% of a resin of BisGMA/TEDGDMA with 1.0 wt-% of PBO is a heat curable and easily moldable (i.e. having low viscosity) composite. The mixture can be cured for example at a pressure pot with a pressure of 5 bar at 100° C., or by compression moulding. The mould can be made of silicone, polytetrafuoroethylene (such as Teflon®), steel etc. A 3-point bending test according to ISO 4049 (2009) of this composite showed a result of 250 MPa, and the structure was essentially nonporous.

Another possible composite mixture having a total filler content 82 wt-% (particles 55 wt % and fibres 27 wt-%) resulted in a thick paste, which was used to impregnate an E-glass rowing, resulting in good handling properties.

Comparative Tests

Comparative tests were preformed using a resin mixture of 70 wt-% UDMA and 30 wt-% TEDGDMA (as above), The inert glass fibres were as above (diameter 6 µm, length 50-200 µm with an average length of 150 µm, i.e. aspect ratio 25) and the particulate fillers were $SiO_2$,BaO (Schott G018-053, surface treated) and had an average diameter of 5 µm. The particulate fillers were thus the same as above but with larger dimensions.

Figure 12:
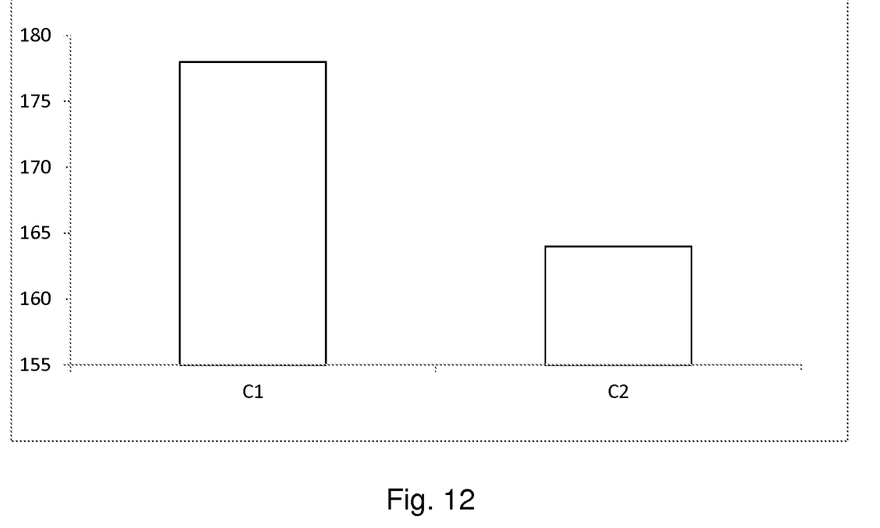
Figure 13:
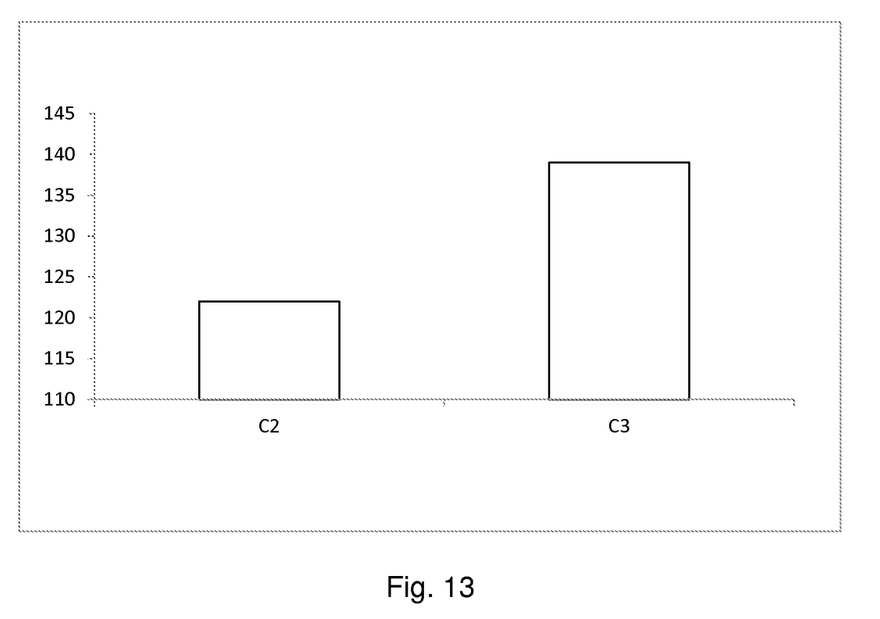

The required extrusion force and the results of the three-point bending test (both measured as above) are given in FIGS. 12 (extrusion force) and 13 (three-point bending test).

In a comparative example C1, the total amount of fillers was 78 wt-%, the rest being resin. Of the fillers, 26 wt-% (of the total weight of the composition) consisted of fibres, the rest being particles. Of the particles, 34 wt-% were particles with an average diameter of 5 µm and 18 wt-% were particles with an average diameter of 0.7 µm.

The required extrusion force for this composition was 178 N (bending strength not measured). The material was thus significantly more difficult to extrude than the present material.

In a comparative example C2, the total amount of fillers was 75 wt-%, of which 25 wt-% were fibres and 25 wt-% particles with an average diameter of 5 µm. The required extrusion force for this composition was 116 N and bending strength was 122 MPa. The material was thus significantly more difficult to extrude than the material according to the present description and had a lower bending strength.

In a comparative example C3 the total amount of fillers was 75 wt-%, of which 25 wt-% were fibres and 25 wt-% particles. Of the particles, 33 wt-% were particles with an average diameter of 5 µm and 17 wt-% were particles with an average diameter of 0.7 µm. The bending strength was 139 MPa, i.e. again significantly lower than was is achieved with the material according to the present invention.

The invention claimed is:

1. A dental material comprising a polymer resin, particulate fillers and randomly oriented inorganic fibres, wherein
   an average largest dimension of the particulate fillers is 0.3-1.2 µm,
   the inorganic fibres have a diameter of 4-8 micrometre and an aspect ratio of 20-80 based on an average length of the inorganic fibres, wherein the average length of the inorganic fibres is 100-200 µm,
   the dental material is void of other fibres,
   the total amount of particulate fillers and inorganic fibres is 70-81 wt-% of the total weight of the material, and
   the amount of inorganic fibres is 20-35 wt-% of the total amount of particulate fillers and inorganic fibres.

2. A dental material according to claim 1, wherein the inorganic fibres are selected from the group consisting of inert glass fibres, bioactive glass fibres, sol gel processed silica fibres, aluminium oxide based fibres, zirconia fibres, apatite fibres, quartz fibres and mixtures thereof.

3. A dental material according to claim 2, wherein the inorganic fibres are inert glass fibres.

4. A dental material according to claim 1, wherein the polymer resin is a methacrylate-based polymer resin.

5. A dental material according to claim 4, wherein the methacrylate-based polymer resin is selected from a group consisting of homopolymers and copolymers of methyl methacrylate, ethyl methacrylate, n-butyl methacrylate, isobutyl methacrylate, 2-ethylhexyl methacrylate, 2-hydroxyethyl methacrylate, cyclohexyl methacrylate, isobornyl methacrylate, tetrahydrofurfuryl methacrylate, benzyl methacrylate, morpholinoethyl methacrylate, acrylic acid, diethylene glycol dimethacrylate, triethylene glycol dimethacrylate, diurethane dimethacrylate, urethane dimethacrylate or 2,2-bis(4-(2-hydroxy-3-methacryloxy)phenyl)-propane.

6. A dental material according to claim 5, wherein the polymer resin is a mixture of urethane dimethacrylate and triethyleneglycol dimethacrylate.

7. A dental material according to claim 6, wherein the polymer resin consists of 65-75 wt-% of urethane dimethacrylate and 25-35 wt-% of triethyleneglycol dimethacrylate.

8. A dental material according to claim 1, wherein the particulate fillers are selected from the group consisting of inert glass, colour pigments inert or bioactive or partially reactive glass ionomer fillers containing elements selected from Si, Al, Ca, P, Ba, Mg, K, Ti, F, Sr, Zn oxides or other compounds of said elements, colour pigments, inter ceramics, hydroxyl apatite or other Ca-phosphates, Al2O3, ZrO2, Ag, Al—Si oxides, feldspar, zerogels, bioactive glasses or filler particles containing functional bioactive or therapeutically active molecules and/or radio-opaque materials.

9. A method for using a dental material according to claim 1 as dental filling material, as prosthodontic material and for manufacturing CAD/CAM blocks to be used in dentistry.

10. A dental material according to claim 1, wherein the amount of inorganic fibres is 20-32 wt-% of the total amount of particulate fillers and inorganic fibres.

11. A dental material according to claim 1, wherein the amount of inorganic fibres is 20-30 wt-% of the total amount of particulate fillers and inorganic fibres.

12. A dental material according to claim 1, wherein the amount of inorganic fibres is 20-27 wt-% of the total amount of particulate fillers and inorganic fibres.

* * * * *